United States Patent [19]
Colin et al.

[11] Patent Number: 4,814,470

[45] Date of Patent: Mar. 21, 1989

[54] TAXOL DERIVATIVES, THEIR PREPARATION AND PHARMACEUTICAL COMPOSITIONS CONTAINING THEM

[75] Inventors: Michel Colin, Thoiry; Daniel Guenard, Montrouge; Francoise Gueritte-Voegelein; Pierre Potier, both of Paris, all of France

[73] Assignee: Rhone-Poulenc Sante, Courbevoie, France

[21] Appl. No.: 73,156

[22] Filed: Jul. 14, 1987

[30]  Foreign Application Priority Data

Jul. 17, 1986 [FR] France ................ 86 10400

[51] Int. Cl.$^4$ ............... A01N 43/02; C07D 305/00
[52] U.S. Cl. ........................... 514/449; 549/510
[58] Field of Search ................ 549/510; 514/449

[56]  References Cited

U.S. PATENT DOCUMENTS 4,206,221  6/1980  Miller et al. ............ 549/510

OTHER PUBLICATIONS

V. Senilh et al, C. R. Acad. Sc. Paris, t. 299, Serie II, No. 15 (1984), pp. 1039–1043.
M. E. Jung et al, Jour. Chem. Soc., Chem. Comm. (1978), pp. 315–316.
R. S. Lott et al, Jour. Chem. Soc., Chem. Comm. (1979), pp. 495–496.
E. Herranz et al, Jour. Am. Chem. Soc., vol. 100:11 (1978), pp. 3596–3598.
Theodora W. Greene, Protective Groups in Organic Synthesis (1981), pp. 223, 225 and 232.

*Primary Examiner*—Glennon H. Hollrah
*Assistant Examiner*—Mark W. Russell
*Attorney, Agent, or Firm*—Stevens, Davis, Miller & Mosher

[57]  ABSTRACT

Taxol derivatives of formula

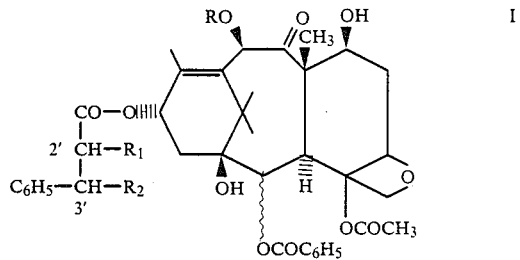

in which R represents hydrogen or acetyl, one of $R_1$ or $R_2$ represents hydroxy and the other represents tert-butoxycarbonylamino and their isomers are useful antitumor agents.

6 Claims, No Drawings

TAXOL DERIVATIVES, THEIR PREPARATION AND PHARMACEUTICAL COMPOSITIONS CONTAINING THEM

The present invention provides new taxol derivatives of formula:

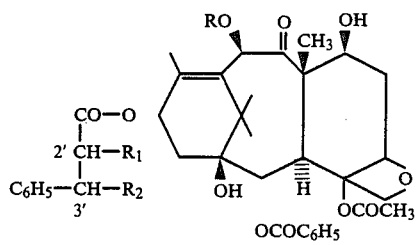

in which R represents hydrogen or acetyl and one of $R_1$ and $R_2$ represents hydroxy and the other represents tert-butoxycarbonylamino and their stereoisomeric forms, and mixtures thereof.

Taxol, which is the formula:

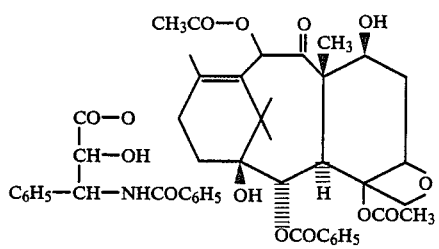

shows remarkable properties, in vitro, of promoting the polymerization of tubulin and inhibiting the depolymerization of microtubules. For this reason, it is a particularly valuable antileukaemia and antitumour agent.

Because of the difficulty of extracting taxol from trunk barks of different species of Taxus (yew), the preparation of derivatives similar to taxol from 10-deacetylbaccatin III, which can be extracted relatively easily from yew leaves, has been proposed. However, the derivatives synthesized until now have shown an activity which is lower than that of taxol [V. Senilh et al., C.R. Acad. Sci., 299, series II, No. 15, p. 1039–1043 (1984)].

It has now been found, and this forms the subject of the present invention, that the products of formula (I) have an activity significantly greater than that of taxol and, a fortiori, greater than that of compounds of formula (I) in which R represents hydrogen, one of $R_1$ or $R_2$ represents hydroxy, and the other represents ethoxycarbonylamino.

According to a feature of the present invention, the products of formula (I) may be obtained by reacting the sodium salt of tert-butyl N-chlorocarbamate with a comound of formula:

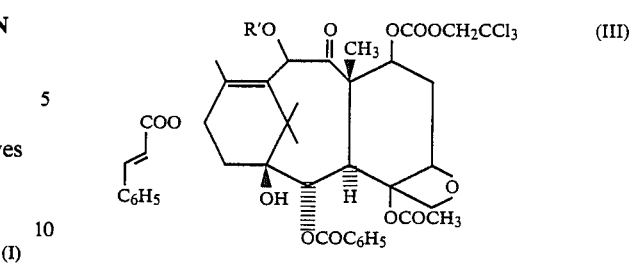

in which R' represents acetyl or 2,2,2-trichloroethoxycarbonyl, in an organic solvent such as acetonitrile in the presence of silver nitrate and a tert-butanol solution of osmium tetroxide at a temperature between 0° and 40° C., followed by the replacement of the 2,2,2-trichloroethoxycarbonyl group(s) in the product of formula:

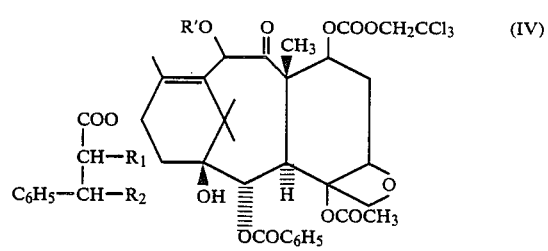

in which R', $R_1$ and $R_2$ are as defined as above, by hydrogen using zinc in the presence of acetic acid at a temperature between 30° and 60° C.

The reaction of the sodium salt of tert-butyl N-chlorocarbamate with a compound of formula (III) leads to a mixture of isomers of the products of formula (IV), the constituents of which may be separated by physicochemical methods such as chromatography.

The sodium salt of tert-butyl N-chlorocarbamate may be prepared from tert-butyl carbamate by the method described in J. Amer, Chem. Soc., 100, 3596 (1978).

The starting materials of formula (III) may be obtained by reacting cinnamoyl chloride, optionally prepared in situ, with the compound of formula:

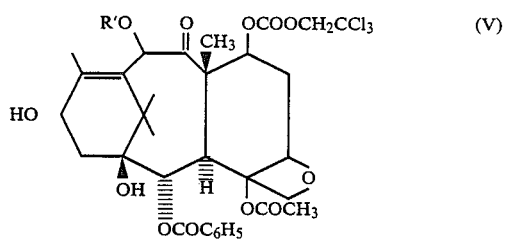

in which R' is as defined above, operating in an anhydrous organic solvent such as toluene in the presence of silver cyanide at a temperature between 80° and 120° C.

The compounds of formula (III) may also be obtained by reacting cinnamic acid with a compound of formula (V) in which R' is as defined above, in an aromatic hydrocarbon such as benzene, toluene or a xylene, in the presence of a condensation agent, such as a carbodiimide, e.g. dicyclohexylcarbodiimide, or a reactive carbonate such as di(2-pyridyl)carbonate, and an activation agent, such as dimethylaminopyridine at a temperature between 60° and 90° C.

For example, while operating in the presence of dicyclohexylcarbodiimide and dimethylaminopyridine, it is particularly advantageous to use a molar excess of cinnamic acid relative to the product of formula (V), the dicyclohexylcarbodiimide being used in a stoichiometric quantity relative to the cinnamic acid and the dimethylaminopyridine being used in a stoichiometric quantity relative to the starting material of formula (V). In general, at least 4 moles of cinnamic acid are used per mole of the compound of formula (V).

The compounds of formula (V) in which R' is as defined above may be obtained by reacting 2,2,2-trichloroethyl chloroformate with baccatin III or with 10-deacetylbaccatin III, in a basic organic solvent such as pyridine, at a temperature between 0° and 50° C. Baccatin III and 10-deacetylbaccatin III are natural products which can be extracted from yew (*Taxus baccata L*) leaves or bark.

The products of general formula (I), and especially those in which R represents hydrogen atom, $R_1$ represents hydroxy and $R_2$ represents tert-butoxycarbonylamino, have valuable biological activities.

Their biological activity may be determined in vitro, using tubulin extracted from pig brain, by the method of M. L. Shelanski et al., Proc. Natl. Acad. Sci. U.S.A., 70, 765–768 (1973). The depolymerization of the microtubules in tubulin may be studied by the method of G. Chauvière et al., C.R. Acad. Sci., 293, series II, 501–503 (1981). In this study, the products of formula (I) were found to be approximately twice as active as taxol.

In vivo, the products of formula (I) were found to be active in mice grafted with leukaemia L 1210 or with leukaemia P 388, at doses of between 1 and 10 mg/kg, administered intraperitoneally. At equitoxic doses, the products of formula (I) showed an antitumour efficacy greater than that of taxol (i.e. an increased survival time, with the animals surviving long-term).

The following Examples illustrate the invention.

EXAMPLE 1

A solution of tert-butyl N-chlorocarbamate sodium salt (0.5 g) and silver nitrate (1 g) in acetonitrile (20 cc) is stirred vigorously for 5 minutes. A solution (0.2 cc) of osmium tetroxide in tert-butyl alcohol (0.1 mole per liter solution), the product of formula (III) in which R' represents a 2,2,2-trichloroethoxycarbonyl radical (2 g) and water (0.16 cc) are then added. After stirring for 20 hours at a temperature in the vicinity of 20° C. and in the absence of light, tert-butyl N-chlorocarbamate sodium salt (0.5 g), the osmium tetroxide solution (0.1 cc) and water (0.06 cc) are added. After stirring vigorously for 48 hours, the reaction mixture is filtered through Celite. The filter is rinsed with acetonitrile and the filtrate is concentrated to dryness. The product obtained is purified by chromatography on silica (Merck 7736 silica), eluting with an ether:hexane (50:50 by volume) mixture and operating under slight pressure. The unreacted product of formula (III) (900 mg) and the oxyaminated products are isolated in this way and the latter are purified and separated by thick layer chromatography, eluting with a methylene chloride:methanol (98:2 by volume) mixture.

The following are thereby obtained:

A product (2'R, 3'S) of general formula (IV) (295 mg) in which R' represents a 2,2,2-trichloroethoxycarbonyl radical, $R_1$ represents a hydroxy radical and $R_2$ represents a tert-butoxycarbonylamino radical, the characteristics of which are as follows:

Specific rotation: $[\alpha]_D^{23} = -38.4°$ (c=1, chloroform).

Ultraviolet spectrum: $\lambda max=231$ nm (15150), $\lambda max=275$ nm (1200), $\lambda max=283$ nm (1035).

Infrared spectrum: main characteristic absorption bands at 3580, 3440, 2960, 1770 and 1730 cm$^{-1}$.

Proton nuclear magnetic resonance spectrum (CDCl$_3$, 400 MHz, shifts in ppm): 1.21 (s, 3H); 1.27 (s, 3H); 1.36 (s, 9H); 1.86 (s, 3H); 1.96 (s, 3H); 2.39 (s, 3H); 2.62 (m, 1H); 3.90 (d, J=7, 1H); 4.17 and 4.32 (2d, J=9, 2H); 4.63 (d, J=3, 1H); 4.59 and 4.90 (2d, J=12, 2H); 4.77 (s, 2H); 4.96 (d, J=9, 1H); 5.27 (dd, J=9 and J=3, 1H); 5.42 (d, J=9, 1H); 5.55 (m, 1H); 5.69 (d, J=7, 1H); 6.21 (t, J=9, 1H); 6.23 (s, 1H); 7.39 (5H); 7.51, 7.62 and 8.09 (5H).

A product (2'S, 3'R) of general formula (IV) (250 mg) in which R' represents a 2,2,2-trichloroethoxycarbonyl radical, $R_1$ represents a hydroxy radical and $R_2$ represents a tert-butoxycarbonylamino radical, the characteristics of which are as follows:

Specific rotation: $[\alpha]_D^{23} = -43.5°$ (c=1, chloroform).

Ultraviolet spectrum: $\lambda max=231$ nm (15300), $\lambda max=275$ nm (1035), $\lambda max=283$ nm (905).

Infrared spectrum: characteristic absorption bands at 3400, 3000, 1770 and 1730 cm$^{-1}$.

Proton nuclear magnetic resonance spectrum (CDCl$_3$, 400 MHz, shifts in ppm): 1.18 (s, 3H); 1.23 (s, 3H); 1.40 (s, 9H); 1.86 (s, 3H); 2.08 (s, 3H); 2.24 (s, 3H); 2.64 (m, 1H); 3.98 (d, J=7, 1H); 4.17 and 4.32 (d, J=9, 2H); 4.48 (d, J=3, 1H); 4.60 and 4.92 (2d, J=12, 2H); 4.78 (s, 2H); 4.97 (d, J=9, 1H); 5.22 (dd, J=9 and J=3, 1H); 5.32 (d, J=9, 1H); 5.58 (m, 1H); 5.70 (d, J=7, 1H); 6.07 (t, J=9, 1H); 6.27 (s, 1H); 7.33–7.45 (5H); 7.48, 7.61 and 8.04 (5H).

A product (2'R, 3'S) of general formula (IV) (250 mg) in which R' represents a 2,2,2-trichloroethoxycarbonyl radical, $R_1$ represents a tert-butoxycarbonylamino radical and $R_2$ represents a hydroxy radical, the characteristics of which are as follows:

Specific rotation: $[\alpha]_D^{23} = -37.8°$ (c=1, chloroform).

Ultraviolet spectrum: $\lambda max=231$ nm (14500), $\lambda max=274$ nm (1730), $\lambda max=282$ nm (1520).

Infrared spectrum: characteristic absorption bands at 3590, 3440, 3000, 1770 and 1730 cm$^{-1}$.

Proton nuclear magnetic resonance spectrum (CDCl$_3$, 400 MHz, shifts in ppm): 1.20 (s, 3H); 1.27 (s, 3H); 1.37 (s, 9H); 1.87 (s, 3H); 2.02 (s, 3H); 2.42 (s, 3H); 2.64 (m, 1H); 3.96 (d, J=7, 1H); 4.19 and 4.32 (2d, J=9, 2H); 4.59 (wide d, J=12, 2H); 4.78 (s, 2H); 4.91 (d, J=12, 1H); 5.00 (d, J=9, 1H); 5.40 (s, 1H); 5.51 (d, J=9, 1H); 5.58 (m, 1H); 5.69 (d, J=7, 1H); 6.25 (s, 1H); 6.31 (t, J=9, 1H); 7.36, 7.40 and 7.46 (5H); 7.48, 7.68 and 8.06 (5H).

And a product (2'S, 3'R) of general formula (IV) (180 mg) in which R' represents a 2,2,2-trichloroethoxycarbonyl radical, $R_1$ represents a tert-butoxycarbonylamino radical and $R_2$ represents a hydroxy radical, the characteristics of which are as follows:

Specific rotation: $[\alpha]_D^{23} = -32°$ (c=1, chloroform).

Ultraviolet spectrum: $\lambda max=231$ nm (14900), $\lambda max=275$ nm (1180), $\lambda max=282$ nm (1050).

Infrared spectrum: characteristic absorption bands at 3600, 3440, 3000, 1770 and 1730 cm$^{-1}$.

Proton nuclear magnetic resonance spectrum (CDCl$_3$, 400 MHz, shifts in ppm): 1.18 (s, 3H); 1.27 (s, 3H); 1.38 (s, 9H); 1.89 (s, 3H); 2.02 (s, 3H); 2.32 (s, 3H);

2.62 (m, 1H); 3.87 (d, J=7, 1H); 4.15 and 4.32 (2d, J=9, 2H); 4.60 (wide d, J=12, 2H); 4.77 (s, 2H); 4.91 (d, J=12, 1H); 4.96 (d, J=9, 1H); 5.16 (d, J=3, 1H); 5.34 (d, J=9, 1H); 5.57 (m, 1H); 5.67 (d, J=7, 1H); 6.16 (t, J=9, 1H); 6.23 (s, 1H); 7.39 (5H); 7.53, 7.66 and 8.07 (5H).

Zinc powder (150 mg) is added to a solution of the product (2'R, 3'S) of general formula (IV) (150 mg) in which R' represents a 2,2,2-trichloroethoxycarbonyl radical, $R_1$ represents a hydroxy radical and $R_2$ represents a tert-butoxycarbonylamino radical, in acetic acid (5 cc). The reaction mixture is stirred for 2 hours at 50° C. and it is then filtered and concentrated to dryness. The residue is taken up with water and extraction is carried out with ethyl acetate. The combined organic phases are concentrated to dryness and the residue is purified by thick layer chromatography, eluting with a methylene chloride:methanol (97:3 by volume) mixture.

A product (2'R, 3'S) of general formula (I) (94 mg) in which R represents a hydrogen atom, $R_1$ represents a hydroxy radical and $R_2$ represents a tert-butoxycarbonylamino radical, the characteristics of which are as follows, is thereby obtained:

Specific rotation: $[\alpha]_D^{23} = -36°$ (c=0.74; ethanol).

Ultraviolet spectrum: λmax=230 nm (14800), λmax=275 nm (1730), λmax=283 nm (1670).

Infrared spectrum: main characteristic absorption bands at 3590, 3440, 1740–1700 cm$^{-1}$.

Proton nuclear magnetic resonance spectrum (CDCl$_3$, 400 MHz, shifts in ppm): 1.12 (s, 3H); 1.24 (s, 3H); 1.35 (s, 9H); 1.77 (s, 3H); 1.87 (s, 3H); 2.28 (m, 2H); 2.37 (s, 3H); 2.58 (m, 1H); 3.91 (d, J=7, 1H); 4.19 and 4.32 (2d, J=9, 2H); 4.26 (m, 1H); 4.62 (d, J=2, 1H); 4.94 (d, J=9, 1H); 5.22 (s, 1H); 5.26 (dd, J=9 and J=2, 1H); 5.46 (d, J=9, 1H); 5.68 (d, J=7, 1H); 6.22 (t, J=9, 1H); 7.38 (5H); 7.50, 7.60 and 8.12 (5H).

Mass spectrum (FAB) m/z: 808 (MH+), 790, 752, 734, 708, 690, 527, 509, 449, 405, 387, 345, 327, 282, 226 and 185.

The product of general formula (III) in which R' represents a 2,2,2-trichloroethoxycarbonyl radical may be prepared according to one of the following methods:

(1) Oxalyl chloride (11.92 cc) is added to a solution of cinnamic acid (9.84 g; 66.5 mmols) in anhydrous toluene (150 cc). The reaction mixture is stirred for 1 hour at 60° C. and the excess oxalyl chloride is then removed by distillation. The cinnamoyl chloride obtained is taken up with anhydrous toluene (300 cc) and the product of general formula (V) (12 g) in which R' represents a 2,2,2-trichloroethoxycarbonyl radical and silver cyanide (7.9 g) are then added. The reaction mixture is heated for 10 hours at 110° C., with vigorous stirring. After cooling, the reaction mixture is filtered and the precipitate is rinsed with ethyl acetate. The combined filtrates are poured into ice-cold water. Extraction is carried out with ethyl acetate. The combined organic phases are concentrated to dryness and then taken up with ether (200 cc). A stream of ammonia is passed through this solution until the ammonium cinnamate formed precipitates. After filtering, the ethereal solution is concentrated and the residue is chromatographed on silica (Merck 7736 silica), eluting with methylene chloride under pressure. The product of general formula (III) (7.6 g) in which R' represents a 2,2,2-trichloroethoxycarbonyl radical, the characteristics of which are as follows, is thereby obtained (yield=55%):

$[\alpha]_D = -56°$ (c=0.567; chloroform).

Ultraviolet spectrum: λmax=217 nm (26800), λmax=222 nm (26900), λmax=232 nm (16100), λmax=276 nm (23600), λmax=283 nm (24400).

Infrared spectrum: main characteristic absorption bands at 3420, 1760, 1725, 1710 and 1635 cm$^{-1}$.

Proton nuclear magnetic resonance spectrum (CDCl$_3$, shifts in ppm): 5.73 (d, J=7, C$_2$H); 3.99 (d, J=7, C$_3$H); 5.02 (d, J=9, C$_5$H); 1.88 and 2.68 (m, 2×C$_6$H); 5.62 (m, C$_7$H); 6.30 (s, C$_{10}$H); 6.21 (t, J=8, C$_{13}$H); 2.48 (m, C$_{14}$H$_2$); 1.29 (s, C$_{16}$H$_3$); 1.23 (s, C$_{17}$H$_3$); 2.16 (s, C$_{18}$H$_3$); 1.88 (s, C$_{19}$H$_3$); 4.20 and 4.34 (d, J=9, 2×C$_{20}$H); 2.31 (acetate); 7.45, 7.60 and 8.07 (benzoate); 6.53 (d, J=16, C$_2$, H); 7.89 (d, J=16, C$_3$, H); 7.45 (4H); 7.60 (1H); 4.62 to 4.93 (d, J=12); 4.79 (s, 2H).

Mass spectrum (chemical ionization) m/z 1023 (MH+), 1005, 831, 813, 683, 665, 491, 431, 369, 309, 291, 149, 131 and 123.

(2) Cinnamic acid (35.52 g; 240 mmols), anhydrous toluene (1 liter), dicyclohexylcarbodiimide (49.44 g; 240 mmols), product of general formula (V) in which R' represents a 2,2,2-trichloroethoxycarbonyl radical (53.5 g; 60 mmols) and dimethylaminopyridine (7.32 g; 60 mmols) are introduced into a 2 liter three-necked round-bottomed flask, equipped with a stirrer and a thermometer, under an argon atmosphere. The mixture is heated for 18 hours at 70° C. under an argon atmosphere. After cooling at 0° C. for 4 hours, the precipitate formed is separated by filtration and then washed with cold toluene (100 cc).

The filtrate is concentrated to dryness and it is then taken up with methylene chloride (1 liter). The solution in methylene chloride is washed with an aqueous 3% (w/v) hydrochloric acid solution (3×150 cc). After concentrating the organic phase, the residue (92 g) is taken up with ethyl ether (500 cc). The solution is allowed to stand at a temperature in the vicinity of 0° C. for 48 hours. The precipitate formed is separated by filtration and washed with ethyl ether at 0° C. The filtrate is concentrated to dryness. A product (89 g) is thereby obtained, which is chromatographed on Merck 7734 silica (2.7 kg), eluting with a toluene:methanol (95:5 by volume) mixture. The product of general formula (III) (58 g) in which R' represents a 2,2,2-trichloroethoxycarbonyl radical is thereby obtained (yield=94.6%).

The product of general formula (V) in which R' represents a 2,2,2-trichloroethoxycarbonyl radical may be prepared as follows:

A solution of 10-deacetylbaccatin III (30 g; 55 mmols) in anhydrous pyridine (480 cc) is cooled under an argon atmosphere to 3° C. 2,2,2-Trichloroethylchloroformate (25.5 cc; 184 mmols) is added in the course of 3 minutes. The reaction mixture is stirred for 3 minutes at 20° C. and then for 6 minutes at 28° C. The solution is then cooled using an ice bath and it is then quickly poured into ice-cold water (1 liter). The aqueous phase is extracted 3 times with methylene chloride (1 liter in total). After concentrating, the pyridine is removed by exhaustive extraction with 1,2-dichloroethane. The crude product obtained (61.9 g) is purified by chromatography on silica (Merck 7736 silica; 1.2 kg), eluting with a methylene chloride:methanol (99:1 by volume) mixture.

The product of general formula (V) (45.6 g) in which R' represents a 2,2,2-trichloroethoxycarbonyl radical, the characteristics of which are as follows, is thereby obtained (yield=93%):

Melting point: 233°–234° C.

Specific rotation: $[\alpha]_D^{23} = -58°$ (c=0.465; chloroform).

Ultraviolet spectrum: $\lambda$max=232 nm (19000), $\lambda$max=276 nm (990), $\lambda$max=283 nm (810).

Infrared spectrum: characteristic absorption bands at 3420, 1765, 1730 and 1720 cm$^{-1}$.

Proton nuclear magnetic resonance spectrum (CDCl$_3$, shifts in ppm): 1.12 (s, 3H); 1.16 (s, 3H); 1.85 (s, 3H); 2.16 (s, 3H); 2.30 (s, 3H); 2.30 (m, 2H); 2.05 and 2.65 (2m, 2H); 4.00 (d, J=7, 1H); 4.18 and 4.35 (2d, J=9, 2H); 4.63 and 4.92 (2d, J=12, 2H); 4.76 and 4.80 (2d, J=12, 2H); 4.92 (t, J=9, 1H); 5.00 (d, J=9, 1H); 5.61 (m, 1H); 5.66 (d, J=7, 1H); 6.30 (s, 1H); 7.50, 7.64 and 8.13 (2t and 1d, J=7, 5H)

Mass spectrum (chemical ionization) m/z 893 (MH+), 875, 701, 683, 579, 387, 327, 309 and 123.

The 10-deacetylbaccatin III may be obtained as follows:

Ground non-dried *Taxus baccata* L leaves (100 kg) are subjected to accelerated percolation, in a rotary device, with 95° alcohol (the true alcohol content of which changes to 80°-85° because of the water contained in the leaves). The first maceration is carried out with alcohol (300 liters) and the subsequent macerations (4×200 liters) are carried out with alcohol recovered by distillation and the alcohol level of which is maintained at 85°. Each percolation lasts for 10 hours and is carried out at a temperature in the vicinity of 20° C. Mixing is ensured by circulating the solvent using a pump.

Each ethanolic phase is concentrated under receded pressure (50-60 mm Hg; 5.4 kPa). The concentrates from each operation (approximately 70 liters), with high water content, are combined and concentrated again to a volume of 20 liters in order to remove the residual alcohol.

The extract, which is not evaporated to dryness, remains in an aqueous medium (20 liters) in the form of a solid suspension. It is taken up with methylene chloride (9 extractions with a total of 100 liters of methylene chloride).

The solution in methylene chloride thus obtained (87 liters), containing the dry extract (2 kg), is concentrated to a volume of 5 liters.

Chromatography is carried out in a 24 cm diameter column containing silica (10.3 kg) (Zeosil: 8 kg; Celite: 2.3 kg).

Successive elutions are carried out, at a flow rate of 8 to 9 liters/hour, with:
  methylene chloride (150 liters) (fraction 1);
  a methylene chloride:methanol (99.5:0.5 by volume) mixture (150 liters) (fraction 2);
  a methylene chloride:methanol (99:1 by volume) mixture (170 liters) (fraction 3) and
  a methylene chloride:methanol (98:2 by volume) mixture (130 liters) (fraction 4).

The first two fractions are combined to give 1.74 kg of dry extract. The third fraction gives 390 g of dry extract. The fourth fraction gives 20 g of dry extract.

The third fraction (390 g), which contains essentially the 10-deacetylbaccatin III, is chromatographed again on silica, eluting with a methylene chloride:methanol (99:1 by volume) mixture, at a flow rate of 4 liters/hour. 4 fractions are thereby obtained, the most useful of which (154 g) gives, after concentrating and digesting in methylene chloride, pure 10-deacetylbaccatin III (22 g).

The mother liquors (132 g), purified by chromatography on silica, give 10-deacetylbaccatin III (8 g).

The total yield of 10-deacetylbaccatin III is 300 mg per kg of leaves.

EXAMPLE 2

Operating as in Example 1, but starting with the product (2'S, 3'R) of general formula (IV) in which R' represents a 2,2,2-trichloroethoxycarbonyl radical, R$_1$ represents a hydroxy radical and R$_2$ represents a tertbutoxycarbonylamino radical, the product (2'S, 3'R) of general formula (I) in which R represents a hydrogen atom, R$_1$ represents a hydroxy radical and R$_2$ represents a tertbutoxycarbonylamino radical, the characteristics of which are as follows, is obtained:

specific rotation: $[\alpha]_D^{23} = -29°$ (c=0.69; ethanol).

Ultraviolet spectrum: $\lambda$max=229 nm (14700), $\lambda$max=275 nm (2350), $\lambda$max=282 nm (2280).

Infrared spectrum: characteristic absorption bands at 3580, 3440, 1740 and 1700 cm$^{-1}$.

Proton nuclear magnetic resonance spectrum (CDCl$_3$-CD$_3$OD, 400 MHz, shifts in ppm): 1.14 (s, 3H); 1.20 (s, 3H); 1.40 (s, 9H); 1.75 (s, 3H); 1.97 (s, 3H); 2.27 (s, 3H); 2.53 (m, 1H); 3.90 (d, J=7, 1H); 4.22 and 4.31 (2d, J=9, 2H); 4.24 (m, 1H); 4.50 (d, J=2, 1H); 5.01 (d, J=9, 1H); 5.19 (d, J=2, 1H); 5.32 (s, 1H); 5.67 (d, J=7, 1H); 6.17 (t, J=9, 1H); 7.26-7.45 (5H); 7.48, 7.62 and 8.07 (5H).

Mass spectrum (FAB) m/z: 808 (MH+), 752, 734, 690, 527, 509, 449, 405, 387, 345, 327, 299, 266 and 185.

EXAMPLE 3

Operating as in Example 1, but starting with the product (2'R, 3'S) of general formula (IV) in which R' represents a 2,2,2-trichloroethoxycarbonyl radical, R$_1$ represents a tert-butoxycarbonylamino radical and R$_2$ represents a hydroxy radical, the product (2'R, 3'S) of general formula (I) in which R represents a hydrogen atom, R$_1$ represents a tert-butoxycarbonylamino radical and R$_2$ represents a hydroxy radical, the characteristics of which are as follows, is obtained:

Specific rotation: $[\alpha]_D^{23} = -29°$ (c=0.47; ethanol).

Ultraviolet spectrum: $\lambda$max=229 nm (16300), $\lambda$max=274 nm (2570), $\lambda$max=282 nm (2380).

Infrared spectrum: main characteristic absorption bands at 3590, 3440, 2990, 1740-1700 cm$^{-1}$.

Proton nuclear magnetic resonance spectrum (CDCl$_3$, 400 MHz, shifts in ppm): 1.12 (s, 3H); 1.22 (s, 3H); 1.35 (s, 9H); 1.77 (s, 3H); 1.91 (s, 3H); 2.27 (m, 2H); 2.38 (s, 3H); 2.59 (m, 1H); 3.96 (d, J=7, 1H); 4.19 and 4.31 (2d, J=9, 2H); 4.25 (m, 1H); 4.58 (dd, J=9 and J=2, 1H); 4.97 (d, J=9, 1H); 5.22 (s, 1H); 5.35 (d, J=2, 1H); 5.48 (d, J=9, 1H); 5.67 (d, J=7, 1H); 6.26 (t, J=9, 1H); 7.35, 7.40 and 7.46 (5H); 7.49, 7.62 and 8.07 (5H).

Mass spectrum (FAB) m/z: 808 (MH+), 790, 752, 734, 708, 527, 509, 449, 405, 387, 345, 327, 282, 226 and 185.

EXAMPLE 4

Operating as in Example 1, but starting with the product (2'S, 3'R) of general formula (IV) in which R' represents a 2,2,2-trichloroethoxycarbonyl radical, R$_1$ represents a tert-butoxycarbonylamino radical and R$_2$ represents a hydroxy radical, the product (2'S, 3'R) of general formula (I) in which R represents a hydrogen atom, R$_1$ represents a tert-butoxycarbonylamino radical and R$_2$ represents a hydroxy radical, the characteristics of which are as follows, is obtained:

Specific rotation: $[\alpha]_D^{23} = -33°$ (c=0.81; ethanol).

Ultraviolet spectrum: λmax=230 nm (14250), λmax=275 nm (1380), λmax=282 nm (1270).

Infrared spectrum: characteristic absorption bands at 3580, 3440, 2900, 1740–1700 cm$^{-1}$.

Proton nuclear magnetic resonance spectrum (CDCl$_3$, 400 MHz, shifts in ppm): 1.12 (s, 3H); 1.22 (s, 3H); 1.36 (s, 9H); 1.72 (s, 3H); 1.94 (s, 3H); 2.32 (s, 3H); 2.51 (m, 1H); 3.85 (d, J=7, 1H); 4.20 and 4.29 (2d, J=9, 2H); 4.22 (m, 1H); 4.58 (dd, J=2 and J=9, 1H); 4.97 (d, J=9, 1H); 5.14 (d, J=2, 1H); 5.22 (s, 1H); 5.65 (d, J=7, 1H); 5.81 (d, J=9, 1H); 6.17 (t, J=9, 1H); 7.37 (5H); 7.50, 7.63 and 8.07 (5H)

Mass spectrum (FAB) m/z: 808 (MH+), 752, 740, 708, 690, 549, 527, 509, 449, 405, 387, 345, 327, 299, 226 and 185.

The present invention also provides pharmaceutical compositions containing a compound of formula (I) in combination with one or more pharmaceutically acceptable, inert or physiologically active, diluents or adjuvants.

These compositions may be presented in any form appropriate for the administration route envisaged. The parenteral route, and especially the intravenous route, is the preferential route for administration.

The compositions according to the invention for parenteral administration may be aqueous or nonaqueous sterile solutions, suspensions or emulsions. Propylene glycol, vegetable oils, especially olive oil, and injectable organic esters, e.g. ethyl oleate, may be used as the solvent or the vehicle. These compositions may also contain adjuvants, especially wetting agents, emulsifiers or dispersants. The sterilization may be carried out in several ways, e.g. using a bacteriological filter, by incorporating sterilizing agents into the composition, by irradiation or by heating. They may also be in the form of sterile solid compositions which may be dissolved or dispersed in sterile water or any other injectable sterile medium.

The products of general formula (I) are more particularly used in the treatment of actue leukaemias and solid tumours, at daily doses which are generally between 1 and 2 mg/kg by the intravenous (perfusion) route for an adult.

The following Example illustrates a composition according to the invention.

COMPOSITION EXAMPLE

The product of formula I obtained in Example 1 (40 mg) is dissolved in Emulphor EL 620 (1 cc) and ethanol (1 cc) and the solution is then diluted by adding physiological saline (18 cc).

This composition may be administered by introduction into an intravenous perfusion of physiological saline given over a period of 1 hour.

We claim:

1. A taxol derivative of formula:

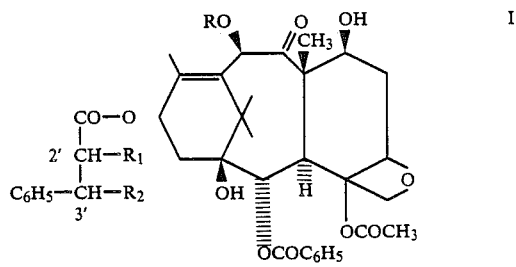

in which R represents hydrogen or acetyl and one of R$_1$ and R$_2$ represents hydroxy and the other represents tert-butoxycarbonylamino, and the stereoisomeric forms thereof and their mixtures.

2. A taxol derivative according to claim 1, in which R is hydrogen, R$_1$ is hydroxy and R$_2$ is tert-butoxycarbonylamino, and having the 2'R, 3'S configuration.

3. A taxol derivative according to claim 1, in which R is hydrogen, R$_1$ is hydroxy, and R$_2$ is tert-butoxycarbonylamino, and having the 2'S, 3'R configuration.

4. A taxol derivative according to claim 1, in which R is hydrogen, R$_1$ is tert-butoxycarbonylamino, and R$_2$ is hydroxy, and having the 2'R, 3'S configuration.

5. A taxol derivative according to claim 1, in which R is hydrogen, R$_1$ is tert-butoxycarbonylamino, and R$_2$ is hydroxy and having the 2'S, 3'R configuration.

6. A pharmaceutical composition which contains a taxol derivative as claimed in claim 1 combined with one or more pharmaceutically acceptable, inert or physiologically active diluents or adjuvants.

* * * * *

UNITED STATES PATENT AND TRADEMARK OFFICE
CERTIFICATE OF CORRECTION

PATENT NO. : 4,814,470                    Page 1 of 4
DATED      : March 21, 1989
INVENTOR(S): Michel COLIN et al.

It is certified that error appears in the above-indentified patent and that said Letters Patent is hereby corrected as shown below:

Column 1, Formula (I):

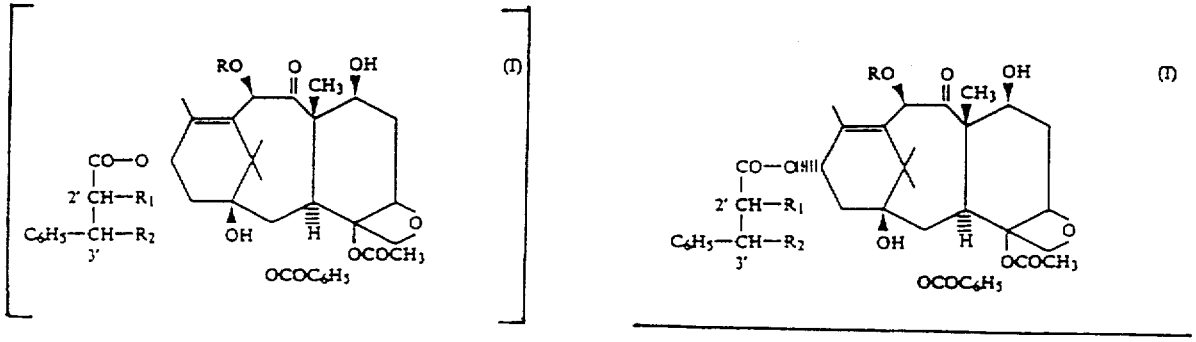

Column 1, Formula (II):

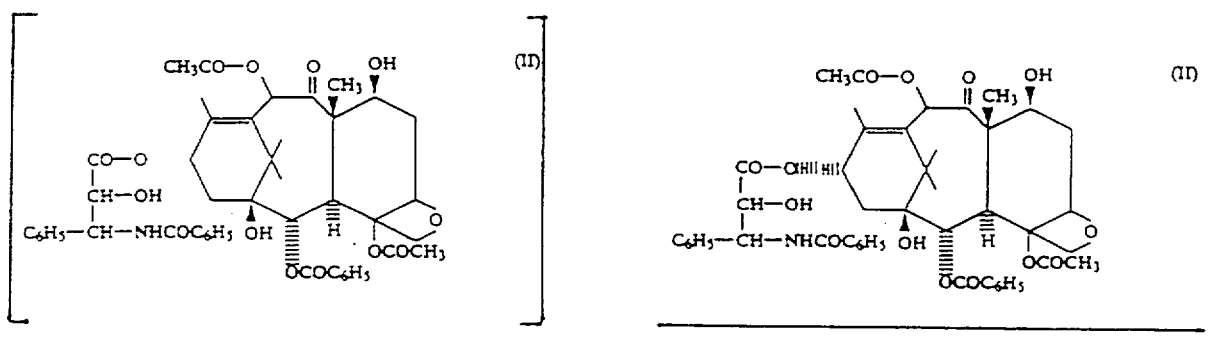

UNITED STATES PATENT AND TRADEMARK OFFICE
CERTIFICATE OF CORRECTION

PATENT NO. : 4,814,470
DATED : March 21, 1989
INVENTOR(S) : Michel COLIN et al.

Page 2 of 4

It is certified that error appears in the above-indentified patent and that said Letters Patent is hereby corrected as shown below:

Column 2, Formula (III):

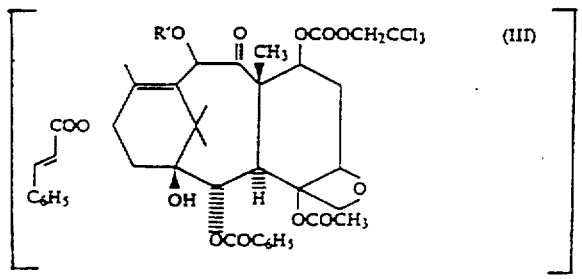 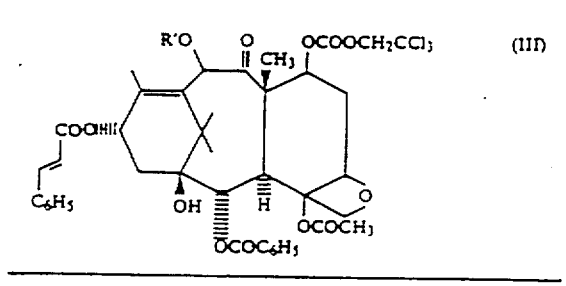

Column 2, Formula (IV):

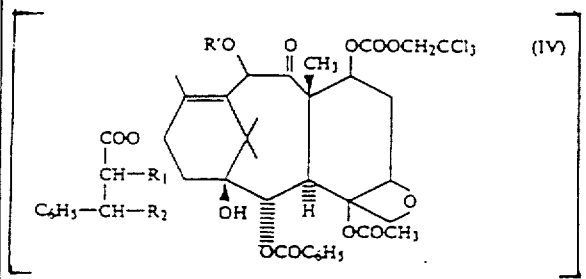 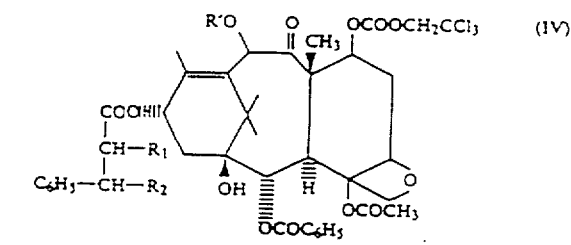

UNITED STATES PATENT AND TRADEMARK OFFICE
CERTIFICATE OF CORRECTION

PATENT NO. : 4,814,470
DATED : March 21, 1989
INVENTOR(S) : Michel COLIN et al.

It is certified that error appears in the above-indentified patent and that said Letters Patent is hereby corrected as shown below:

Column 2, Formula (V):

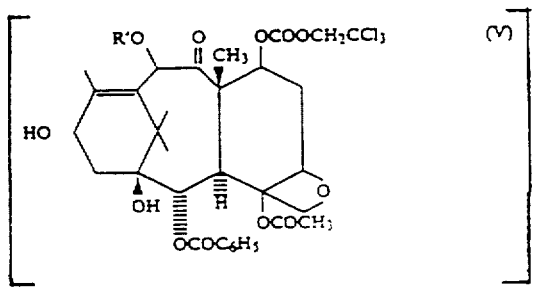 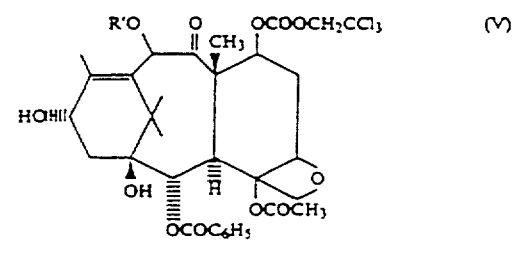

UNITED STATES PATENT AND TRADEMARK OFFICE
CERTIFICATE OF CORRECTION

PATENT NO. : 4,814,470
DATED : March 21, 1989
INVENTOR(S) : Michel COLIN et al.

It is certified that error appears in the above-indentified patent and that said Letters Patent is hereby corrected as shown below:

IN THE CLAIMS:

Claim 1, please amend the formula as follows:

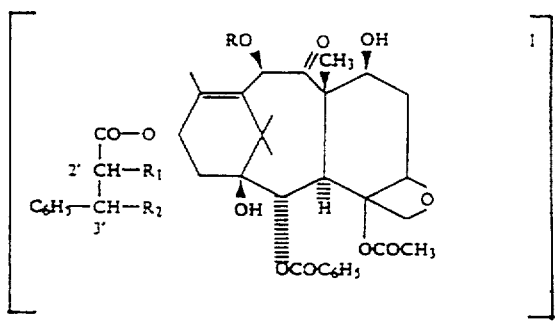 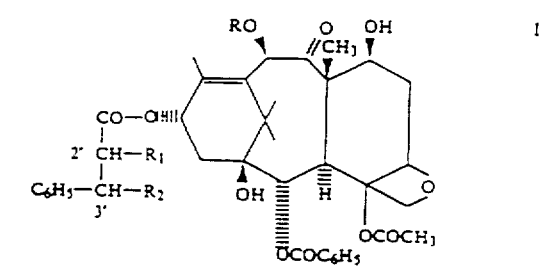

Signed and Sealed this

Twenty-ninth Day of October 1996

Attest:

BRUCE LEHMAN

Attesting Officer

Commissioner of Patents and Trademarks

UNITED STATES PATENT AND TRADEMARK OFFICE

CERTIFICATE EXTENDING PATENT TERM
UNDER 35 U.S.C. § 156

PATENT NO.      :   4,814,470

ISSUED          :   March 21, 1989

INVENTOR(S)     :   Michel Colin et al.

PATENT OWNER    :   Rhone-Poulenc Rorer S.A.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,035 days from July 14, 2007, the original expiration date of the patent, with all rights pertaining thereto as provided by 35 U.S.C. § 156(b).

I have caused the seal of the Patent and Trademark Office to be affixed this 20th day of November 1997.

Bruce A. Lehman
Assistant Secretary of Commerce and
Commissioner of Patents and Trademarks